United States Patent
Averbuch

(10) Patent No.: US 9,595,131 B2
(45) Date of Patent: Mar. 14, 2017

(54) IMAGE VIEWING APPLICATION AND METHOD FOR ORIENTATIONALLY SENSITIVE DISPLAY DEVICES

(71) Applicant: COVIDIEN LP, Mansfield, MA (US)

(72) Inventor: Dorian Averbuch, Ramat Hasharon (IL)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 14/693,556

(22) Filed: Apr. 22, 2015

(65) Prior Publication Data

US 2015/0228116 A1    Aug. 13, 2015

Related U.S. Application Data

(63) Continuation of application No. 13/047,725, filed on Mar. 14, 2011, now Pat. No. 9,111,386.
(Continued)

(51) Int. Cl.
*G06T 15/20* (2011.01)
*G06F 3/0481* (2013.01)
(Continued)

(52) U.S. Cl.
CPC .............. *G06T 15/20* (2013.01); *A61B 34/20* (2016.02); *G06F 3/04815* (2013.01);
(Continued)

(58) Field of Classification Search
CPC ................... G06T 15/08; G06T 19/00; G06T 2207/30004; G06T 2210/41; G06T 2219/028; G06T 2219/008; G06T 2219/2016; A61B 6/466; A61B 8/523; G06F 3/017; G06F 19/321; G06F 2203/04808; G06F 2203/04104; G06F 3/04845; G06F 3/0488
See application file for complete search history.

(56) References Cited

U.S. PATENT DOCUMENTS 7,386,339 B2    6/2008    Strommer et al.
8,521,252 B2    8/2013    Diez
(Continued)

FOREIGN PATENT DOCUMENTS

CN    1617173 A    5/2005
JP    09-204162 A    8/1997
(Continued)

OTHER PUBLICATIONS

Japanese Office Action and Translation for JP 2013-537661 dated Nov. 17, 2015.
(Continued)

*Primary Examiner* — Haixia Du

(57) ABSTRACT

A system and method for presenting three-dimensional image volume data utilizing an orientationally-sensitive display device whereby the image volume is navigable simply by tilting, raising and lowering the display device. Doing so presents an image on the screen that relates to the angle and position of the display device such that the user gets the impression that the device itself is useable as a window into the image volume, especially when the device is placed on or near the source of the image data, such as a patient.

20 Claims, 6 Drawing Sheets

Related U.S. Application Data

(60) Provisional application No. 61/409,495, filed on Nov. 2, 2010.

(51) Int. Cl.
| | | |
|---|---|---|
| *G06T 15/08* | (2011.01) | |
| *G06T 19/00* | (2011.01) | |
| *G06T 13/20* | (2011.01) | |
| *G06T 15/50* | (2011.01) | |
| *A61B 34/20* | (2016.01) | |
| *A61B 34/00* | (2016.01) | |

(52) U.S. Cl.
CPC .............. *G06T 13/20* (2013.01); *G06T 15/08* (2013.01); *G06T 15/506* (2013.01); *G06T 19/00* (2013.01); *G06T 19/003* (2013.01); *A61B 34/25* (2016.02); *A61B 2034/107* (2016.02); *A61B 2034/2048* (2016.02); *A61B 2034/2051* (2016.02); *A61B 2034/2055* (2016.02); *G06T 2215/12* (2013.01); *G06T 2215/16* (2013.01); *G06T 2219/2016* (2013.01)

(56) References Cited

U.S. PATENT DOCUMENTS

| | | | |
|---|---|---|---|
| 8,745,536 B1 * | 6/2014 | Davidson | G06F 3/04815 |
| | | | 715/702 |
| 9,111,386 B2 | 8/2015 | Averbuch | |
| 2002/0140666 A1 | 10/2002 | Bradski | |
| 2002/0140698 A1 | 10/2002 | Robertson et al. | |
| 2003/0073907 A1 | 4/2003 | Taylor | |
| 2003/0234797 A1 | 12/2003 | Williams et al. | |
| 2005/0203367 A1 | 9/2005 | Ahmed et al. | |
| 2006/0173268 A1 | 8/2006 | Mullick et al. | |
| 2008/0207997 A1 | 8/2008 | Higgins et al. | |
| 2008/0269596 A1 | 10/2008 | Revie et al. | |
| 2009/0171355 A1 * | 7/2009 | Amis | A61B 17/1714 |
| | | | 606/53 |
| 2009/0221908 A1 | 9/2009 | Glossop | |
| 2010/0005391 A1 | 1/2010 | Fukuda et al. | |
| 2010/0008555 A1 | 1/2010 | Trumer et al. | |
| 2010/0121190 A1 | 5/2010 | Pagoulatos et al. | |
| 2010/0174421 A1 | 7/2010 | Tsai et al. | |
| 2011/0285622 A1 | 11/2011 | Marti et al. | |

FOREIGN PATENT DOCUMENTS

| | | |
|---|---|---|
| JP | 10-051711 A | 2/1998 |
| JP | 2000-155855 A | 6/2000 |
| JP | 2001-005522 A | 1/2001 |
| JP | 2001-338037 A | 12/2001 |
| JP | 05-266145 B2 | 8/2013 |
| WO | 9420924 A1 | 9/1994 |

OTHER PUBLICATIONS

PCT International Search Report from corresponding application PCT/US2011/028412 dated May 5, 2011.
Chinese Office Action for CN 2011-80061055.8 dated Jan. 27, 2015.
Japanese Office Action for JP 2013-537661 dated Mar. 10, 2015.
Australian Official Action for AU 2011/324017 dated Jun. 22, 2015.
Canadian Office Action for Canadian Appln. No. 2,816,801 dated Oct. 27, 2015.
Cassinelli, Alvaro et al., "Volume slicing display", ACM Siggraph Asia 2009 Art Gallery & Emerging Technologies: Adaptation On. Siggraph Asia '09, Dec. 19, 2009, pp. 88-89.
Spindler, Martin et al., "Exploring information spaces by using tangible magic lenses in a tabletop environment", CHI 2010: Media Showcase—Video Night, Apr. 10-15, 2010, Atlanta, GA, pp. 4771-4776.
Supplementary Partial European Search Report issued in corresponding Application No. EP 11838376 dated Dec. 19, 2016, 9 pages.

* cited by examiner

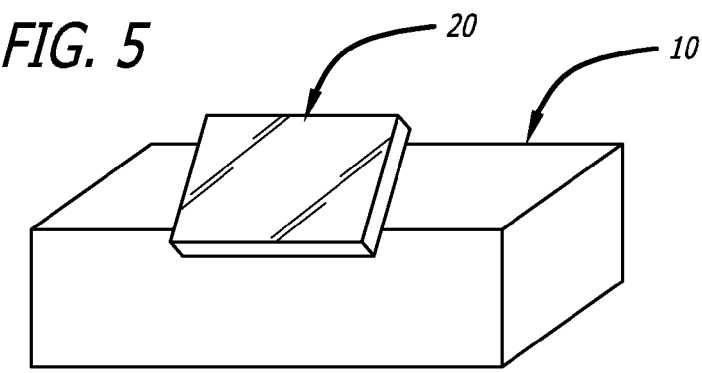
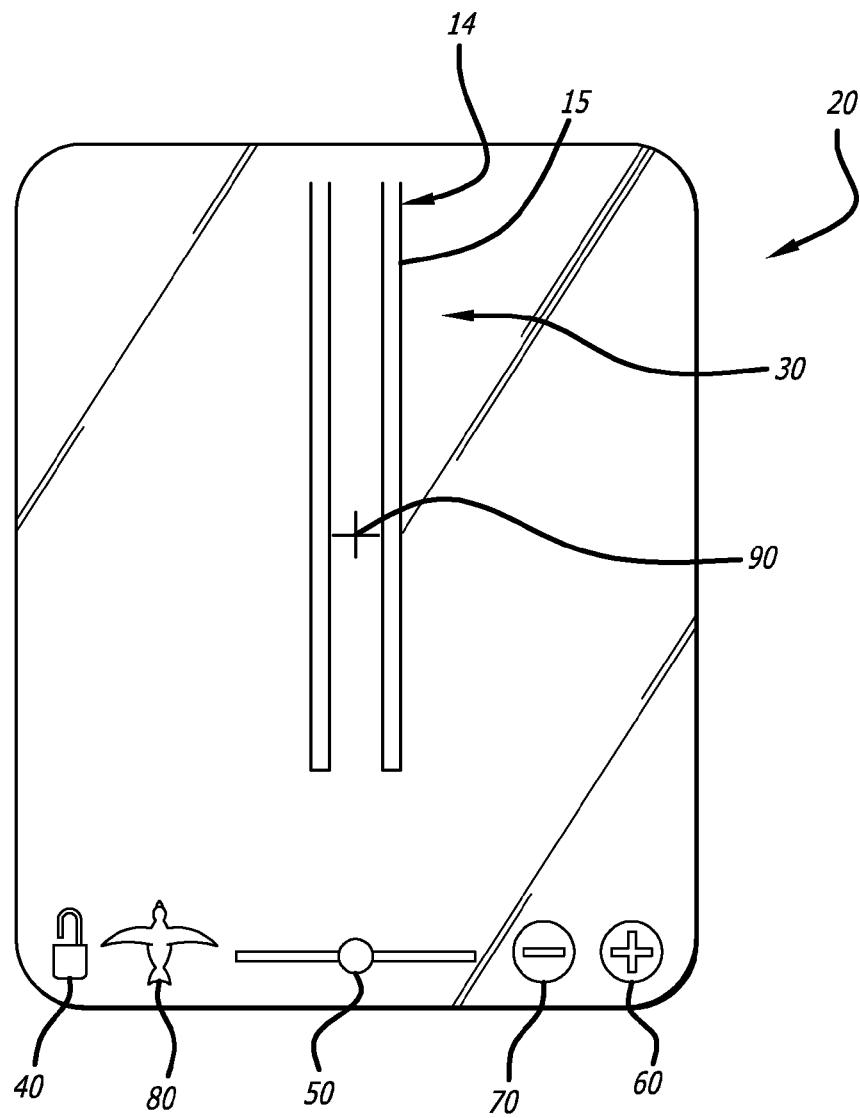

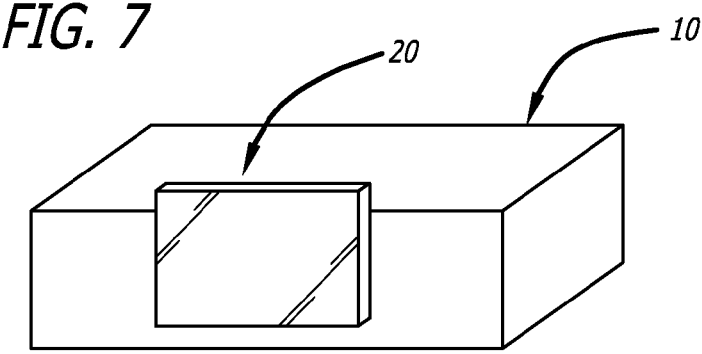
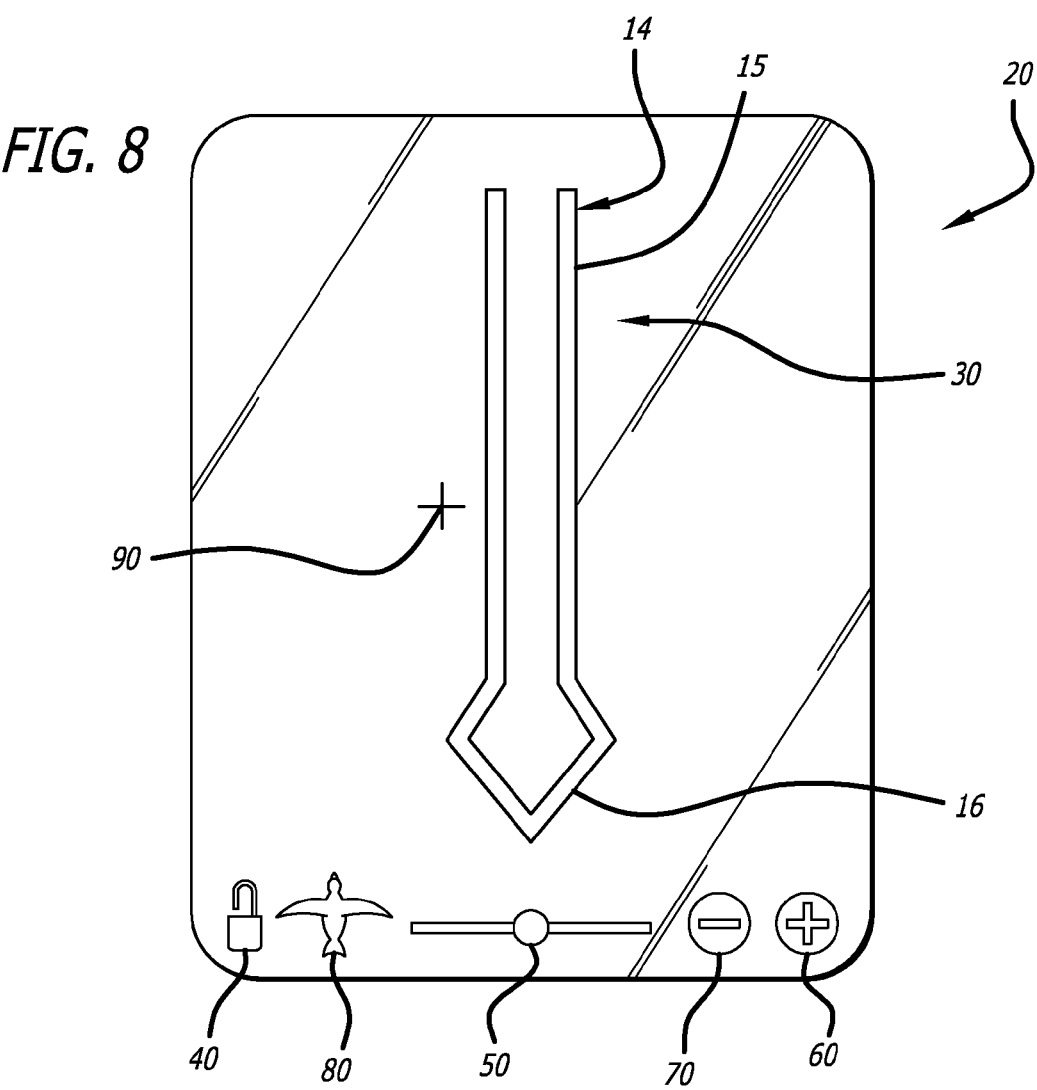

IMAGE VIEWING APPLICATION AND METHOD FOR ORIENTATIONALLY SENSITIVE DISPLAY DEVICES

RELATED APPLICATIONS

This application is a continuation application of U.S. patent application Ser. No. 13/047,725, filed on Mar. 14, 2011, the entire contents of which are hereby incorporated herein by reference, which claims priority to U.S. Provisional Application Ser. No. 61/409,495 filed Nov. 2, 2010, which is hereby incorporated herein by reference in its entirety.

SUMMARY OF THE PRESENT INVENTION

The present invention provides an intuitive application for viewing complex, three-dimensional, image volumes using existing devices that include accelerometer Gyroscope or other location and\or orientation sensing technology, such as smart phones, iPads®, and the like. Doing so provides users, such as physicians, surveyors, engineers, and the like, with the advantages these intuitive devices provide.

It is envisioned that this application could be used with an unlimited variety of imaged objects. Non-limiting examples include medical patients, manufactured objects, animals, geological structures such as oil wells, volcanoes, and fault lines, computer-rendered hypothetical structures, etc. Throughout this application, when clarity dictates an example be used, a medical patient will be referenced. This is not meant to imply that the present invention is more applicable to medical patients and should not be so construed.

One aspect of the present invention provides an application uses the orientation sensing aspect of the display device and localization if applicable to the specific device to automatically change the display based on the orientation of the device. Doing so creates the illusion that the device itself can actually see into the source of the 3D volume, for example, a patient. The displayed images remain aligned with the actual patient regardless of the orientation of the device. Thus, if the device is held horizontally above the patient, the display is a plan view of the patient, aligned in an x-y plane, such that the display appears as though the device is an x-ray machine. If the device is rotated vertically and held on the side of the patient, a side elevation of the patient is displayed. Preferably, the display continuously changes as the orientation of the device changes, to remain aligned with the patient.

Another aspect of the present invention is a planning capability, whereby the device can efficiently be used to identify and mark a target, such as a lesion or other area of interest, for future reference.

Another aspect of the present invention provides a program that allows a user to plan a navigation pathway to a selected target. The navigation pathway planning feature preferably relies on natural spatial information loaded into the three-dimensional image data or segmented as part of preprocessing of the image data, to assist in automatically providing a logical, least obtrusive, pathway to the target.

Yet another aspect of the present invention provides a corresponding internal virtual image option. The user is able to select the virtual view as needed to aid in visualization. Preferably, as part of the pathway feature, a fly-through option is also provided, while user has unique ability to learn the pathway through real time interaction with its display during fly-through.

Thus, the present invention provides a method of displaying images on an orientationally-sensitive display device comprising: providing three-dimensional image volume data to said device relating to an object; registering a location and orientation of said device with said object; displaying on said display device an image generated using said data corresponding to said location and orientation of said device; generating new images corresponding to changes in location and orientation of said device relative to said object; wherein said correspondence between displayed generated images and said object give an impression to a user that said device is seeing into said object.

Registering a location and orientation of said device with said object may comprise placing at least one marker on said object and tracking a position of said device relative to said at least one marker.

Tracking a position of said device relative to said at least one marker may comprise using an optical tracking mechanism to locate said markers.

Tracking a position of said device relative to said at least one marker may comprise using a magnetic positioning system.

Registering a location and orientation of said device with said object may comprise using a global positioning system incorporated into said device, said global positioning system providing locations of said object and said device.

A preferred method of the present invention may also comprise giving the user the option to lock the present image such that further moving of said device does not result in a changing of said image until desired.

A preferred method of the present invention may also comprise providing an option to said user to plan a desired path through said object.

A preferred method of the present invention may also comprise providing a fly-through feature whereby, when selected, an animated representation of said desired path is displayed from a viewpoint along said path.

The present invention also provides method of presenting three-dimensional image volume data relating to an object comprising: accessing said three-dimensional image volume data using an orientationally-sensitive display device; registering a location and orientation of said device with said object; displaying on said display device an image generated using said data corresponding to said location and orientation of said device; continuously generating new images corresponding to changes in location and orientation of said device relative to said object; wherein said correspondence between displayed generated images and said object give an impression to a user that said device is seeing into said object.

Registering a location and orientation of said device with said object may comprise placing at least one marker on said object and tracking a position of said device relative to said at least one marker.

Tracking a position of said device relative to said at least one marker may comprise using an optical tracking mechanism to locate said markers.

Tracking a position of said device relative to said at least one marker may comprise using a magnetic positioning system.

Registering a location and orientation of said device with said object may comprise using a global positioning system incorporated into said device, said global positioning system providing locations of said object and said device.

A preferred method may also comprise giving the user the option to lock the present image such that further moving of said device does not result in a changing of said image until desired.

A preferred method may also comprise providing an option to said user to plan a desired path through said object.

A preferred method may also comprise providing a fly-through feature whereby, when selected, an animated representation of said desired path is displayed from a viewpoint along said path.

The present invention also provides a system for use in presenting internal images of an object comprising: an orientationally-sensitive display device; three-dimensional image volume data relating to said object accessible by said device; and a computer program executable by said device that receives input from orientation sensors of said device, as well as registration data between a location and orientation of said device relative to a location and orientation of said object, and generates on a display of said display device, an internal image of said object that corresponds to said location and orientation of said display device relative to said object, such that it appears to a user that he or she is looking through the display device into the object.

A preferred embodiment of the system of the present invention may also include a computer program that updates said internal image of said object that corresponds to said location and orientation of said display device relative to said object whenever movement of said display device is detected.

A preferred embodiment of the system of the present invention may also include a computer program that provides an option to lock said image of said object such that movement of said device does not result in a changed image.

A preferred embodiment of the system of the present invention may also include a slider feature that, when moved, causes said device to generate image changes that correspond to a hypothetical movement along an axis that is normal to a plane of said display screen.

A preferred embodiment of the system of the present invention may also include a fly-through feature whereby, when selected, generates an animated representation of said desired path is displayed from a viewpoint along said path.

BRIEF DESCRIPTION OF THE FIGURES

FIG. 5 depicts a device using the application of the present invention being held in an orientation relative to the volume of FIG. 2;

FIG. 6 is an embodiment of a screenshot of the application of the present invention as would be seen on the device of FIG. 5;

FIG. 7 depicts a device using the application of the present invention being held in an orientation relative to the volume of FIG. 2;

FIG. 8 is an embodiment of a screenshot of the application of the present invention as would be seen on the device of FIG. 7;

DETAILED DESCRIPTION OF THE PREFERRED EMBODIMENTS

The present invention provides a software application for use with display devices that incorporate a position-sensing and/or orientation-sensing technology, such as accelerometers or gyroscopes, for example. Non-limiting examples of such devices include Apple® devices such as the iPad® and iPhone®. It is to be understood that the screenshots described herein are merely non-limiting examples used to convey the general concept of the present invention, and that though some of the specific features discussed herein may be claimed as part of the present invention, the manner in which they are depicted in the screenshots is not meant to be limiting.

Figure 1:
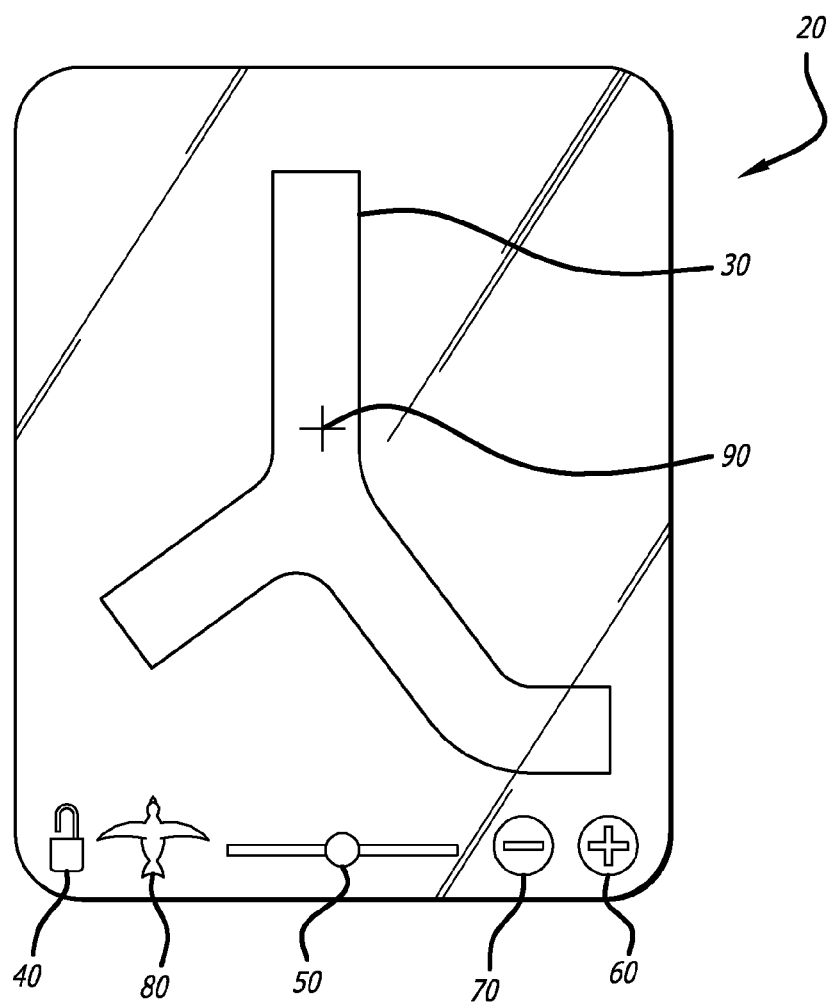
FIG. 1 is an embodiment of a screenshot of the application of the present invention.

Referring now to the figures, and first to FIG. 1, there is shown a screenshot of a device running an embodiment of the application 20 of the present invention. The screenshot includes an image 30, as well as user controls 40, 50, 60, 70 and 80.

Image 30 is a two-dimensional slice of a three-dimensional volume of image data that has been taken using an imaging technology such as CT, MRI, fluoroscopy, for example. As is well-known in the art, a plurality of two-dimensional parallel scans, such as CT scans for example, can be taken and compiled into a data volume. Once compiled, that volume can be used to create two-dimensional image slices that do not correspond to specific scans, but are geometrically accurate depictions of the contents of the volume nonetheless. Hence, a user can use the volume to view a slice in virtually any plane contained in the volume.

Figure 2:
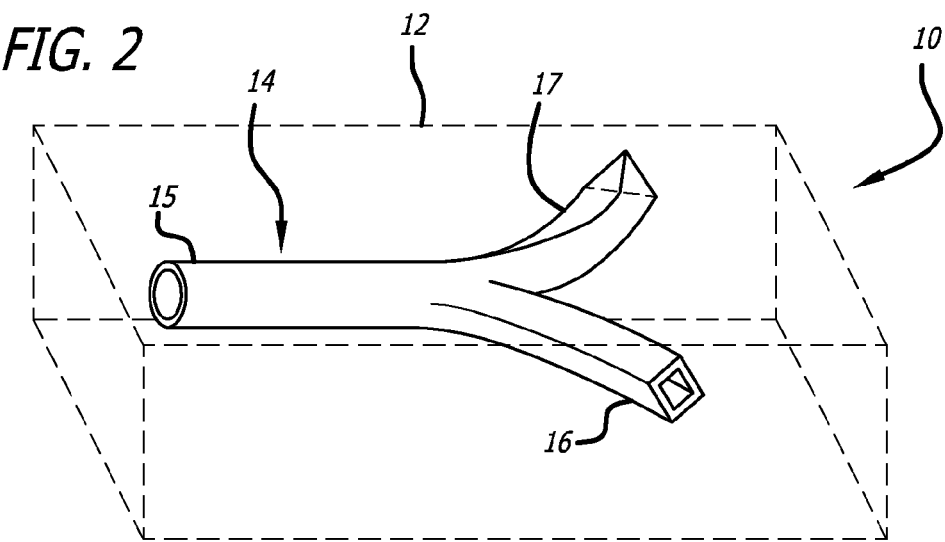
FIG. 2 is a simplified drawing of a three-dimensional volume having an internal geometry for use in describing the present invention.

In order to clearly explain the application of the present invention, an extremely simplified model of a three-dimensional volume is depicted in FIG. 2. The volume 10 includes imaging boundaries 12 depicted as dotted lines. These lines 12 represent the extents of the volume imaged. Within the image is a tubular network 14 that includes three branches 15, 16 and 17. Branch 15 has a circular cross-section, branch 16 has a diamond-shaped cross-section, and branch 17 has a triangular cross-section. These varying cross-sections are providing merely for clarity. Though such three-dimensional image volumes are known, the application of the present invention marries such imaging technology with the aforementioned, orientationally sensitive display technology, to create a virtual X-ray device. The magnitude of this innovative leap is evidenced by the seemingly simplistic, yet powerful user controls.

Control 40 is shaped like a padlock, and can be toggled between a locked and unlocked position. When in the unlocked position, shown, the image 30 changes constantly as the device 20 is tilted. Some embodiments, described below, also provide a changing image when the device is moved laterally or vertically. To be clear, based on the orientation sensitivity of the device launching the application of the present invention, the image changes fluidly and continuously with the tilting of the device 20. It does not merely toggle between orthogonal positions.

When control 40 is in the locked position, the image 30 remains still. This is useful when the image displays something of interest and it is desired to maintain the image while moving the device 20, such as to confer about the image with someone other than the primary user.

Control 50 is a slide control that allows the user to change the image 30 in an axis that is perpendicular to the present plane of the device 20. In one embodiment, the image changes automatically when tilted, but based on the type of orientation sensor used by the device, may not change when the device 20 is lifted or lowered along a normal axis to the device. Slide control 50 allows for this change. If the device 20 includes gyroscopic technology, for example, this feature may automatically occur as the device is moved along the normal axis. A slide control 50 may still be desired, however. For example, one embodiment allows the slide to be used even when the control 40 is in the locked position. This allows a user to set the device 20 on a table and scroll "up and down" through the object without moving the device.

Control 60 is a landmark/waypoint marking feature. It allows a user to add a mark to the image 20 in order to identify a feature. It is used in conjunction with the crosshairs 90, located in the middle of the display. Preferably, the display is a touchscreen. As such, the crosshairs 90 can be moved relative to the image 30 by simply sliding a finger across the display. In one embodiment, the crosshair 90 may be placed anywhere on the display. In another embodiment, the image may be moved around "under" the crosshairs, which remain centered on the display. Either way, once the crosshairs 90 are placed over a location of interest on the image 30, the control 60 may be depressed to place a landmark on that location.

Control 70 is a landmark/waypoint delete feature. It simply deletes or unmarks a previously marked location. In one embodiment, it works by deleting a last location on the first press, and a second to last location on a second press, and so on. In another embodiment, the crosshairs 90 are placed over an existing landmark and the button 70 is touched, thereby allowing landmarks to be deleted in any order.

Control 80 is a fly-through feature. Once a pathway to a target is planned (as described below) touching the control 80 changes the image 30 to a virtual model of the three-dimensional volume. The display thus shows a realistic, perspective view that provides the user the experience of flying through a lumen (for example in the case of a vascular or bronchial imaging volume) from a logical starting point to the target. This feature would provide a physician with an expected view as though the physician were looking through an endoscope. In a preferred embodiment, a graphic of the bird flies from the button itself to the starting point of the image 30, swoops downward and then the view is converted to a virtual image. This way, the user sees exactly where the journey begins.

It is understood that the controls discussed herein are merely an example set and that they may be changed based on the use of the application. For example, it is envisioned that the application be used in a firefighting capacity, to provide firefighters with a virtual, real-time three dimensional map of a building, thereby providing them with a lighted display of where they are despite being in a smoke-filled environment. In such an application, various communication controls may be provided that allow the firefighter to send communications to an outside user with the touch of a button, rather than having to rely on audible communications equipment. Such an application would also benefit from being linked to a second device, such that an observer on the outside of the building would be able to see the same image 30 as the user inside the building.

Figure 3:
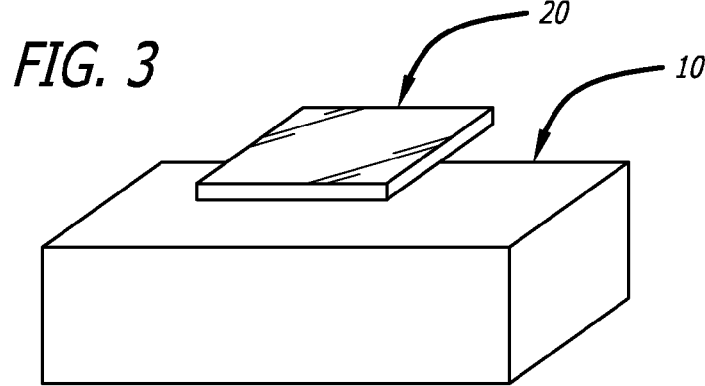
FIG. 3 depicts a device using the application of the present invention being held in an orientation relative to the volume of FIG. 2.
Figure 4:
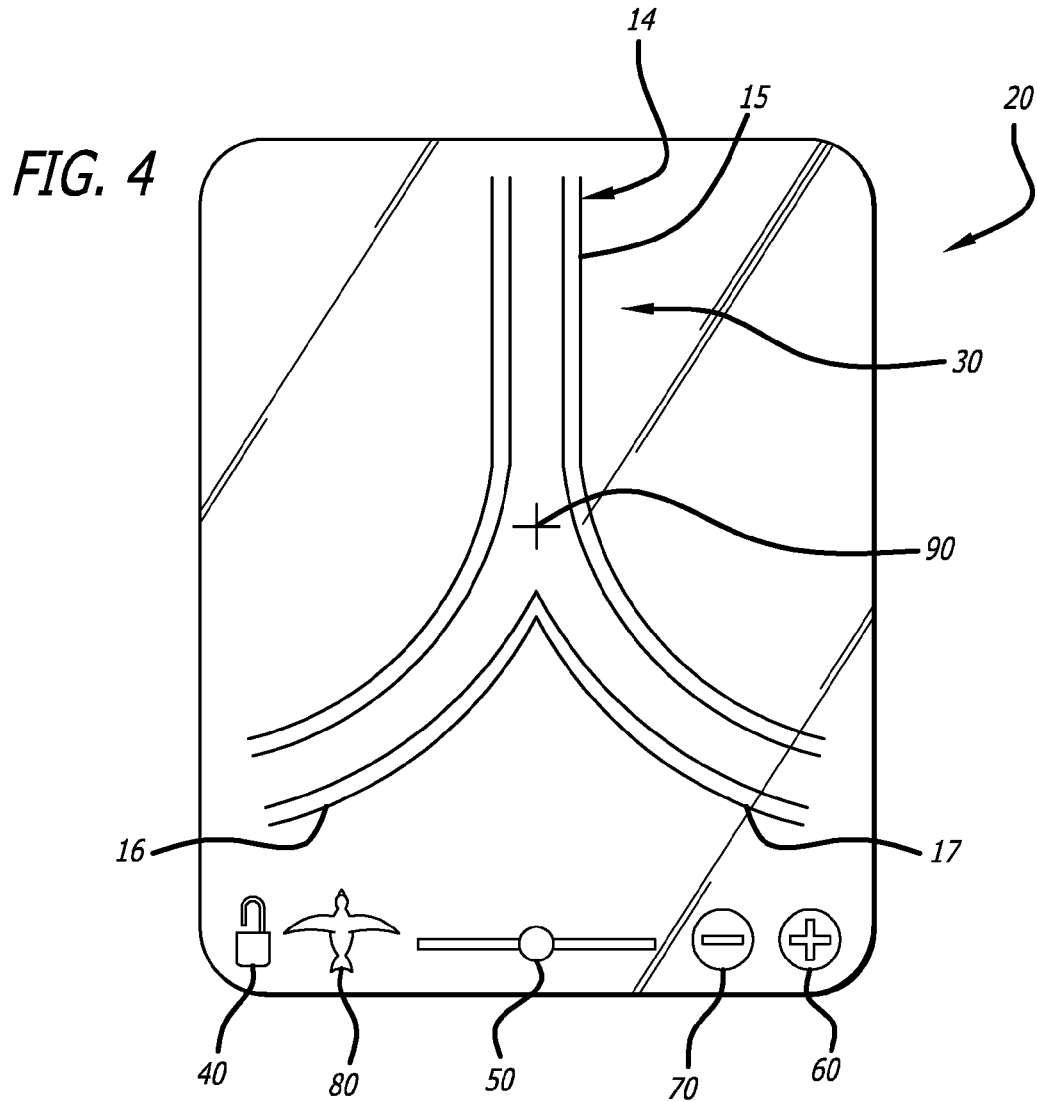
FIG. 4 is an embodiment of a screenshot of the application of the present invention as would be seen on the device of FIG. 3.

FIGS. 3-8 provide examples of what a user might see on the display 20 when viewing the volume 10 shown in FIG. 2 from various angles. Referring first to FIGS. 3 and 4, there is shown in FIG. 3 the position of the display 20 relative to the volume 10. It can be seen that the display 20 is being held in a horizontal orientation above the volume 10. FIG. 4 shows the image 30 that results from being held in the orientation of FIG. 3. It can be seen that the image 30 is a horizontal cross-section through the tubular network 14.

In FIG. 5, the display has been tilted slightly along a longitudinal axis. FIG. 6 shows the resulting image 30.

In FIG. 7, the display has been tilted further so that it is now vertically oriented. FIG. 8 shows the resulting image.

Figure 9:
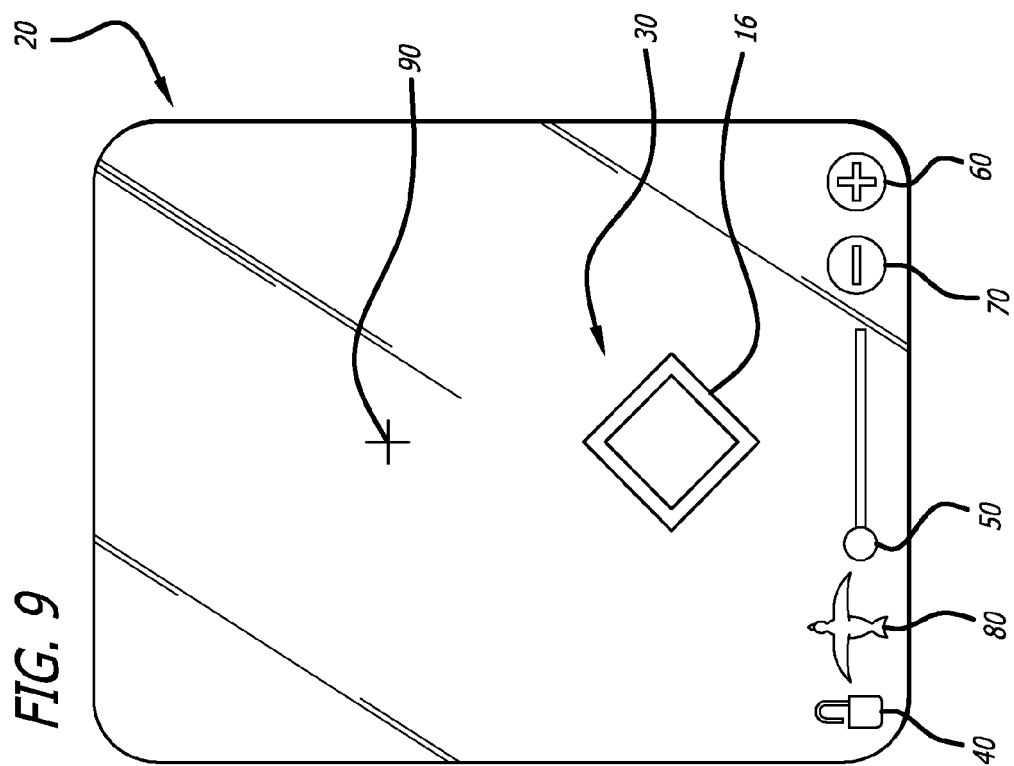
FIGS. 9-11 show embodiments of screen shots that would result from varying the setting of the slider control as would be seen on the device of FIG. 7; and, FIG. 12 shows an embodiment of a screenshot of the application of the present invention being used for pathway planning.
Figure 10:
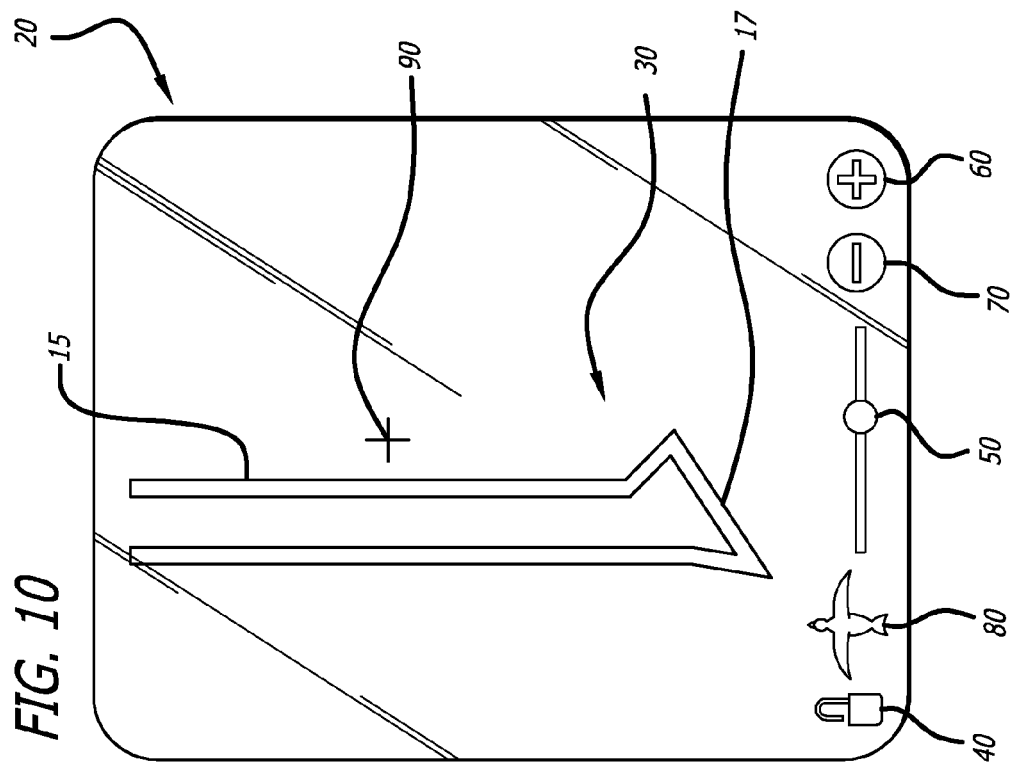
Figure 11:
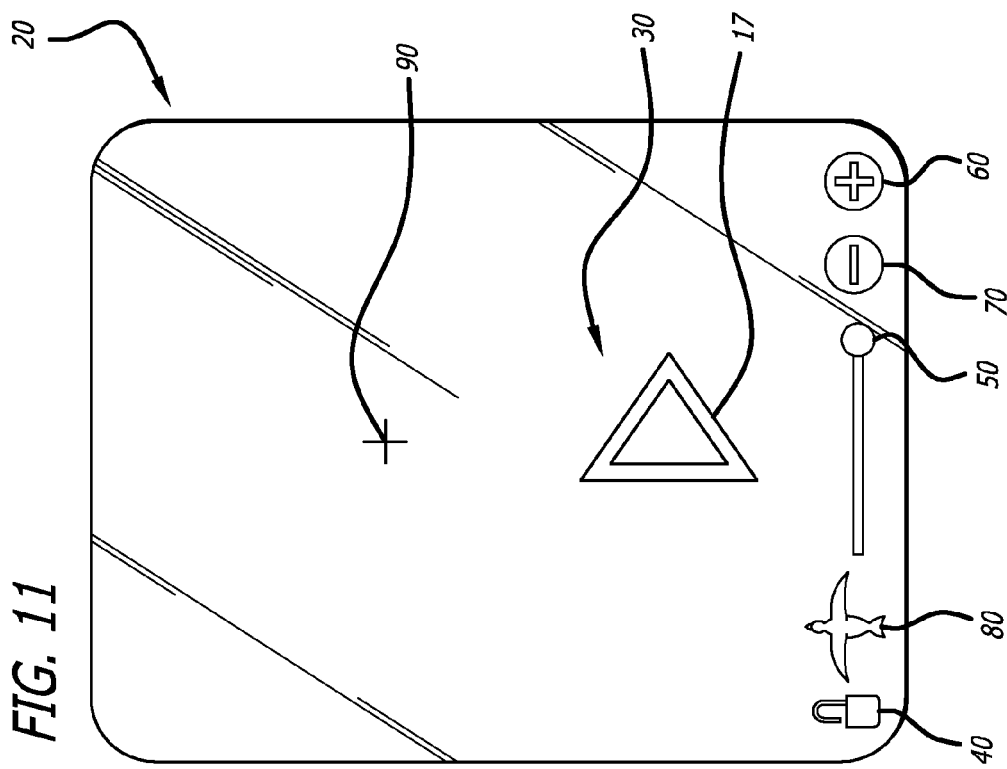

FIGS. 9-11 illustrated the use of the slider control 50. Still using the relative orientation of the display 20 shown in FIG. 7, FIG. 9 shows the resulting image 30 when the slider is in a left-most position. Doing so places the resulting image 30 in a position closest to the display. FIG. 10 shows the slider moved to the right, and FIG. 11 shows the slider moved to the right even further.

As stated previously, an alternative to the slider 50 is an embodiment whereby the relative position between the device 20 and the volume (object) 10 is monitored or somehow accounted for. In other words, the device 20 is registered with the volume or object 10. One way to accomplish registration is with one or more sensors or markers on the volume 10. The device 20 may track its position relative to the sensors or markers using an optical device or a magnetic positioning system. Alternatively, in the case of larger volumes, such as a geological volume or a building, a global positioning system may be used. It is also possible that a device 20 use precise gyroscopic technology such that, once the device 20 is registered with the volume 10, the gyroscopic abilities of the device 20 continuously track the relative position of the device 20 in relation to the volume 10. It is envisioned that a periodic re-registering would be desired to prevent an accumulation of compounded errors.

Figure 12:
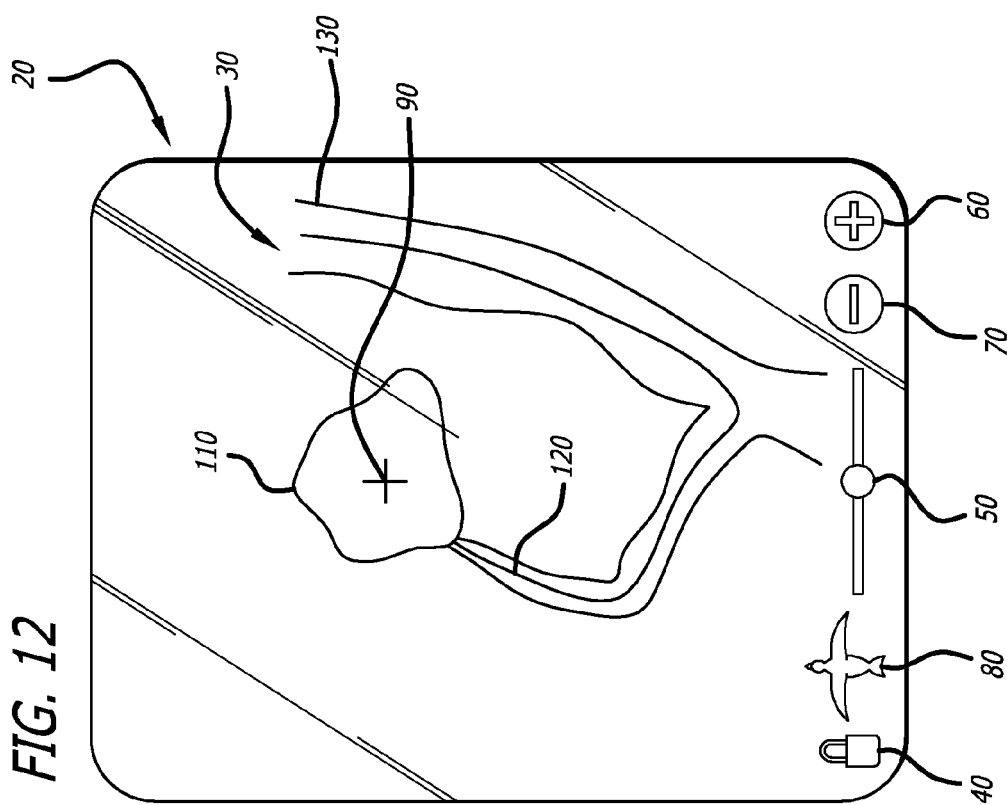

The present invention also includes a pathway planning feature. Referring now to FIG. 12, there is shown a display 20 of an image 30 of a hypothetical, simplified patient lung. The physician has identified a lesion 110 and moved the image relative to the crosshairs 90 such that the crosshairs 90 are centered on the lesion. Preferably, the physician has tilted the device 20 in several different angles to ensure that the crosshairs 90 are approximately in the volumetric center of the lesion 110.

The physician then touches the lock control 40 to fix the image 30. With the crosshairs 90 in the preferred location, the physician touches the add waypoint/landmark control 60. If the physician does not like the position of the crosshairs 90, the delete control 50 may be touched.

Next the physician marks a second point 120 in the airways. In one embodiment this is accomplished by sliding the image using the touchscreen until the crosshairs are located over the desired point 120. Because the lock 40 is active, the image does not change if the relative position of the device 20 and the volume (not shown in FIG. 12) are changed. However, the image may be moved relative to the crosshairs 90. In another embodiment, the crosshairs 90 may be repositioned anywhere on the display 20. Once satisfied with the second position 120, the physician then touches the add control 60 again and not only is the second position 120 marked, but an algorithm automatically illuminates the pathway all the way to a procedure entry point, in this case the trachea 130. One can see that this same pathway planning could be used in other applications such as mine rescues, firefighting, etc.

One aspect of the present invention provides an image volume access system that uses a scanning technology, such as an optical reader, in conjunction with a wireless data base access capability, to upload an appropriate image volume into the device for a given case or patient. For example, a physician making rounds could carry a single display device 20. Upon reaching a patient, the physician could use the device 20 to scan a marker on the patient or in the patient's record, to upload an image volume of an area of interest inside the patient. This ensures that the correct image volume is loaded into the device.

It is further envisioned that the device 20 be usable with certain, real-time imaging technology, such as electromagnetic position and orientation sensing systems available on medical probes. By registering the device 20 with the volume 10 and/or the electromagnetic system (not shown), a real-time image of a probe may be superimposed onto the image 30.

It is further envisioned that a laser indication system could be incorporated with the device in medical or other settings to show exactly the plane of the image 30 relative to the volume 10. For example, even when the image 30 is registered with the volume 10, it requires an amount of speculation to judge how deep the plane is into the volume 10. This is because the display 10 cannot be inserted into the volume 10 in applications such as medical applications. However, a ceiling and/or wall mounted laser beam could be used to illuminate a line on the patient showing exactly the plane of the image 30.

One application of the present invention of particular interest is a medical diagnostic application whereby 3D imaging data is loaded into the device 20. A physician, using the application of the present invention, may then use the device 20 to review the image data from various angles with unprecedented speed. This application may be performed in or outside the present of the object (patient). In the event that the physician is reviewing the images without the presence of the patient, there would be no registration necessary between the device 20 and the patient.

Presently, image data is reviewed one slide at a time when diagnostic analysis is performed. The physician relies on memory to see the differences between successive slides in order to mentally compile the slides into a vision of what the area of interest looks like in three dimensions. This process is very time consuming and requires exceeding concentration on the part of the physician. Using the present invention, the physician can move the device around from various angles to not only "flip through" thousands of slides, back and forth, but by angling the device, new views are generated by the device that never existed previously as slides. Hence, a dynamic, fluid evaluation of a ct scan is made possible that is unprecedented.

The present invention has been described herein using mere examples. It is to be understood, however, that the possible real world applications of the present invention are almost endless and the descriptions provided are in no way meant to be limiting. The only limitations to the scope of the present invention are to be interpreted from the claims set forth below.

What is claimed is:

1. A method of displaying images on a screen of a display device, which is orientationally sensitive, the method comprising:

providing three-dimensional image volume data relating to an object to the display device;

displaying on the screen of the display device a slice image of the object generated from the three-dimensional image volume data based on a location and an orientation in a coordinate system for the three-dimensional image volume data, wherein the location and the orientation in the coordinate system correspond to a location and an orientation of the display device in a real space, respectively, wherein the slice image is a geometrically reconstructed two dimensional image from the 3D volume by slicing the 3D volume according to the orientation at the location;

displaying a target sign over the slice image;

detecting a sliding input on the screen of the display device;

generating new slice images based on changes in the location and orientation of the display device with respect to the coordinate system for the three-dimensional image volume data and based on the sliding input; and displaying an indication of a plane of the displayed slice image with respect to the coordinate system for the three-dimensional image volume data, wherein, when the new slice images are generated based on the sliding input, the new slice images are generated based on a location of the target sign over the slice image and a direction of the sliding input.

2. The method of claim 1, further comprising allowing a user to continuously view the object in three dimensions, from a plurality of angles, in real-time, as the display device moves based on the location and orientation in the coordinate system corresponding to the location and the orientation of the display device.

3. The method of claim 1, further comprising marking at least a portion of a pre-planned path within the three-dimensional image volume data with a plurality of markers.

4. The method of claim 3, further comprising marking the pre-planned path from an entry point in the three-dimensional image volume data to a target identified by a user.

5. The method of claim 4, further comprising automatically illuminating the pre-planned path in response to placement of the plurality of markers.

6. The method of claim 1, further comprising registering the location and the orientation of the display device in the real space to the location and orientation in the coordinate system.

7. The method of claim 6, further comprising registering the location and orientation of the display device by placing at least one marker on the object and tracking a position of the display device relative to the at least one marker.

8. The method of claim 7, further comprising tracking the location of the display device relative to the at least one marker by an optical tracking mechanism.

9. The method of claim 7, further comprising tracking the position of the display device relative to the at least one marker by a magnetic positioning system.

10. The method of claim 1, further comprising locking a present slice image in place such that the present slice image is maintained when the display device further moves.

11. The method of claim 1, further comprising displaying an animated representation of a pre-planned path from a viewpoint along the pre-planned path when a fly-through feature is selected.

12. The method of claim 1, further comprising causing the display device to generate another slice image based on the orientation the display device, wherein the another slice image is obtained from the three-dimensional image volume data at a depth along an axis normal to the orientation in the coordinate system and the depth corresponds to a movement of a slider bar.

13. A system for use in presenting internal images of an object, the system comprising:
a display device, which is orientationally sensitive;
three-dimensional image volume data relating to the object accessible by the display device;
a computer program executable by the display device for:
receiving input from orientation sensors of the display device;
displaying on a screen of the display device a slice image of the object based on a location and an orientation in a coordinate system for the three-dimensional image volume data, wherein the location and the orientation in the coordinate system correspond to a location and an orientation of the display device in a real space, respectively;
displaying a target sign over the slice image;
detecting a sliding input on the screen of the display device;
generating new slice images based on changes in the location and orientation of the display device with respect to the coordinate system for the three-dimensional image volume data and based on the sliding input, wherein the slice image is a geometrically reconstructed two dimensional image from the 3D volume by slicing the 3D volume according to the orientation at the location; and
displaying on the display of the display device an indication of a plane of the displayed slice image with respect to the coordinate system for the three-dimensional image volume data,
wherein, when the new slice images are generated based on the sliding input, the new slice images are generated based on a location of the target sign over the slice image and a direction of the sliding input.

14. The system of claim 13, wherein a user continuously views the object in three dimensions, from a plurality of angles, in real-time, as the display device moves based on the location and orientation in the coordinate system corresponding to the location and the orientation of the display device.

15. The system of claim 13, wherein the displayed slice image includes at least a portion of a pre-planned path marked with a plurality of markers by a user.

16. The system of claim 15, wherein the pre-planned path is marked from an entry point in the three-dimensional image volume data to a target identified by the user.

17. The system of claim 16, wherein the pre-planned path is automatically illuminated in response to placement of the plurality of markers.

18. The system of claim 13, wherein the location and the orientation of the display device is registered to the location and the orientation in the coordinate system by placing at least one marker on the object and by tracking a position of the display device relative to the at least one marker.

19. The system of claim 13, further comprising a slider that, when moved, causes the display device to generate another slice image based on the orientation of the display,
wherein the another slice image is obtained from the three-dimensional image volume data at a depth along an axis normal to the orientation in the coordinate system and the depth corresponds to a movement of the slider.

20. The system of claim 13, further comprising a fly-through feature that, when selected, displays an animated representation of a pre-planned path from a viewpoint along the pre-planned path.

* * * * *